United States Patent [19]
Fleckenstein

[11] Patent Number: 6,068,743
[45] Date of Patent: May 30, 2000

[54] BRAIN-PO$_2$ MEASURING DEVICE

[76] Inventor: Wolfgang Fleckenstein, Eiderweg 14, 24247 Mielkendorf, Germany

[21] Appl. No.: 09/117,127
[22] PCT Filed: Feb. 13, 1997
[86] PCT No.: PCT/EP97/00669
§ 371 Date: Jul. 22, 1998
§ 102(e) Date: Jul. 22, 1998
[87] PCT Pub. No.: WO97/29681
PCT Pub. Date: Aug. 21, 1997

[30] Foreign Application Priority Data

Feb. 16, 1996 [DE] Germany ............... 196 05 739

[51] Int. Cl.[7] .................................................. G01N 27/404
[52] U.S. Cl. ......................... 204/402; 204/406; 204/415
[58] Field of Search .................................. 204/402, 431, 204/432, 415, 406

[56] References Cited

U.S. PATENT DOCUMENTS

| | | | |
|---|---|---|---|
| 4,532,013 | 7/1985 | Dietz et al. | 204/402 |
| 4,705,617 | 11/1987 | Beebe et al. | 204/402 |
| 4,950,378 | 8/1990 | Nagata | 204/402 |
| 5,352,349 | 10/1994 | Inamoto et al. | 204/402 |

FOREIGN PATENT DOCUMENTS

| | | |
|---|---|---|
| 91/09302 | 6/1991 | WIPO . |
| 93/06776 | 4/1993 | WIPO . |

OTHER PUBLICATIONS

Fujito Yuko et al, *Galvanic Cell Type Oxygen Sensor*, European Patent Office, Patent Abstracts of Japan, pub. No. 60093343 of May 25, 1985, appl. 58201973 filed Oct. 27, 1983, Japan Storage Battery Co. Ltd.

*Primary Examiner*—T. Tung
*Attorney, Agent, or Firm*—Walter C. Farley

[57] ABSTRACT

A measuring device for determining the oxygen partial pressure in human brain tissue has a probe (5) with a tube (7) of tissue-compatible plastic material in a measuring region surrounding an electrolyte-filled volume (8). Immersed in the electrolyte, which contains acetate, is a polaragraphic cathode (11) with a limited exposed surface and an anode (13). The tube is oxygen permeable in the measuring region. The electrodes are electrically connected to a measuring apparatus which applies a DC voltage at a first polarity to the electrodes (11, 13) and determines a measuring current using a measuring amplifier. A regenerating device causes the electrodes to be supplied with a regenerating voltage reversed from the first polarity for times and at current magnitudes based on the measurement current and duration.

2 Claims, 3 Drawing Sheets

BRAIN-PO₂ MEASURING DEVICE

FIELD OF THE INVENTION

The invention relates to measuring apparatus to determine the partial oxygen pressure in human brain tissue using a probe having a thin flexible tube made of a tissue-compatible plastic enclosing a volume filled with electrolyte and housing a polaragraphic cathode and an anode, the tube being oxygen permeable at least in a measurement zone, the probes being connected to a measuring apparatus.

BACKGROUND OF THE INVENTION

From the following documents, namely

German periodical Acta Neurochir. 1993 (Suppl.) 59, pp 50–57;

page 51 and under the title "Brain Tissue $pO_2$ Measuremerts", further

German periodical Medizintechnilc 110 vol 2. 1990, pp 44–53 (special issue)

and

Acta Neurochirurgica 1992 (Suppl.) 59, pp 50–57 it is known to perform measurements directly in the brain tissue using a thin flexible catheter probe of the Clark type.

From the following documents, namely

Periodical Biotelemetry Patient Monitoring 1979, pp 16–31 and

German Periodical Proceedings Dtsch. Ges. Biomed. Techn. (1973), pp 29, 30

"Sauerstoffsensoren für in-vivo Messungen" ["Oxygen sensors for in-vivo measurements"], W. Mundt, very thin and highly flexible tubular catheters are known which form a Clarik type $pO_2$ probe suitable for this purpose.

Using appropriate emplacement techniques such as are described in the post-published patent application DE 195 02 183.5, such probes can be freely placed in the brain. Because of their small diameters and high flexibilities, such probes are suitable for long-term measurements in the brain tissue and in other susceptible body tissues. They are able to follow tissue movement (pulse, breathing) without hampering such movements and apply only slight pressure effects on the surrounding tissue, and as a result the oxygen supply is not adversely affected in the measurement process.

On the other hand, such extremely thin probes have drawbacks because their slight dimensions affect the implementability of long-term measurements.

Typically, a probe of the above type has an inside diameter of a few tenths of a mm and a length of several tens of cm. Consequently, the inner space to be filled with electrolyte is of the order of a few $mm^3$, of which however only a small portion is available in the zone of the tiny cathode surface Such a small electrolyte supply is unusually low for $PO_2$ probes of the Clark type and this constitutes a drawback for long-term measurements.

Clark type $pO_2$ probes subject an electrolyte space to the ambient oxygen by means of an oxygen diffusion membrane. The oxygen diffuses through the membrane against the diffusion impedance. The quantity of oxygen per unit time entering the electrolyte depends on the ambient partial oxygen pressure. The entering oxygen is reduced by two electrodes, namely a cathode made of a suitable noble metal and an anode typically of silver, optionally with a silver oxide surface. The resulting current (measuring apparatus current) unambiguously depends on the in-diffusing oxygen, that is the ambient partial oxygen pressure. An appropriate polarographic potential must be applied to the electrodes.

Salt solutions, usually sodium chloride, are used as the electrolyte. Hydroxide is generated in the reduction of oxygen. Anodic silver goes into solution as silver salt. Silver is indeed amply present at the anode. On the other hand, the tiny supply of electrolyte of the probes being discussed is consumed comparatively quickly. The electrochemical equilibria change, and the relationship between the measuring current and the incoming flow of oxygen changes. When this occurs, the measurement must be stopped and the probe must be replaced. Electrolyte replenishment at the site, that is in the tissue, is impossible.

The problem of electrolyte consumption is described for probes of this kind in the German periodical Laborpraxis, July–August 1984, pp 736–739

"Ein neues Sauerstoff-Meβsystem" [A new oxygen measuring system] Klaus Rommel and a 3-electrode configuration is proposed to solve this problem, which however is unsuited for probes used in the brain because of the required minute diameter and high flexibility, and moreover such a system can only sense the electrolyte consumption but not eliminate it.

A medical $pO_2$ probe is known from the British periodical

Medical and Biological Engineering and Computing, 30, 1992, pp 121–122 which while basically operating on the Clark principle on the other hand does not comprise the membrane rigorously permeable only to gases, but a polyurethane membrane. This material is water-permeable, as indeed required in this design, in order to soak the electrolyte salt which is present in dry form under the membrane. Because the membrane, however, is also ion-permeable, the probe responds to the ambient pH and measuring is possible only at constant ambient pH. Therefore, the measurements are to be carried out in a phosphate buffered solution. This probe is poorly suited for medical purposes because it responds to ambient, fluctuating pH and moreover may release salts from its electrolyte supply to the outside and thereby may damage the tissue.

A probe used in sugar determination in a biological environment is known from

U.S. Pat. No. 4,950,378 calling for an enzyme converting sugar into $H_2O_2$ by means of an intrinsic probe operating on the Clark principle. Poisoning of the cathode surface takes place in this probe and can be eliminated by temporary operation at reversed polarity. This probe is free of electrolyte-supply problems.

SUMMARY OF THE INVENTION

An object of the present invention is to provide a measuring apparatus of the above type which, using a conventional Clark probe and a membrane permeable only to gases and requiring only a minute supply of electrolyte, allows substantial measurement times.

In accordance with the invention, the regenerating mode may be turned on after an operating mode during which only so little electrolyte has been used that the measurement parameters still are unchanged. Regeneration then takes place with a regenerating current in a direction opposite from that of the measuring current which reverses the chemical reactions that tool, place during measuring, thus regenerating the electrolyte. Silver again deposits on the anode which, during regeneration, acts as a cathode, though it will always be denoted herein as the anode, and again there is generation of the electrolyte salt and oxygen which diffuses out through the diffusion membrane. Once the initial conditions have been reestablished, measuring can be performed again. In this, manner, without withdrawal of the probe and its attendant brain degradations, very long measurements (weeks) can be carried out that are interrupted only by the regeneration intervals. The electrolyte will always be adequately regenerated during measurement and the probe therefore operates at stable, reliable parameters, that is, it offers reliable measurement values. Switching to regeneration and back to measurement can be carried out manually or automatically at selected time intervals. The invention is especially well suited for the highly sensitive brain tissue through it also may be used in other, highly sensitive body tissues. The electrolyte supply is an acetate.

These salts, illustratively sodium or potassium salts, offer the advantage over the conventional halide salts that the silver salts produced in the course of measurement are substantially more soluble than silver halide salts. For that reason, regeneration achieves nearly complete renewed separation of the silver as the basis of correspondingly high electrolyte regeneration.

By providing an electrolyte having a proper mixture of acetate, acetic acid and. phosphate, in a known manner, use is made of the buffering of the salt/acid mixture in order to keep within safe limits the rise in pH caused by oxygen reduction and affecting the measurement parameters of the probe.

For Clark probes having substantial electrolyte supplies and used for short measurement times, anodes with surfaces of silver oxide or silver salt (electrode of the second kind) are preferred. In these electrodes, however, the measurement parameters depend on the concentrations of the electrolyte anions. As regards the probe of the above species with a minute supply of electrolyte and long measurement times, a pure silver anode (electrode of the first kind) is preferred, because it is free of this dependence, and therefore makes it possible to measure with stable probe parameters over substantial time.

It is impossible to externally ascertain the electrolyte conditions, for instance chemically or electrically, that is, the time at which the electrolyte has been consumed to such an extent that switching to the reverse mode is mandatory. This determination would be possible only with special test equipment already precluded because of bulkiness of the probes of the types described. The electrolyte consumption can be determined form the time of measurement and the measuring current, illustratively from the integral of current over time. An accurate measurement of the actual consumption of electrolyte is then obtained and the time when the probe leaves the predetermined range of parameters on account of excessive electrolyte consumption and must be regenerated can be precisely determined. Accordingly, the measuring apparatus can switch over automatically at optimally long times of measurement between regenerating intervals.

The data medium associated with the probe may store further probe parameters such as data concerning its manufacture, serial number, calibration data, patient information and the like and in particular also the time and variations of the measuring current during the preceding time of measurement. If, midway in a measurement, the probe is disconnected from the measuring apparatus and hooked-up to another, then the latter can proceed with the measurement until the admissible electrolyte consumption has been reached and switch to the regenerating mode only then. This feature is advantageous in many instances when the probe must be disconnected from the measuring apparatus, for instance when washing the patient and especially when moving the patient into another bed. In that case, the measuring apparatus need not be carried along, but instead an apparatus at the new bed may be used.

DESCRIPTION OF PREFERRED EMBODIMENTS

Figure 1:
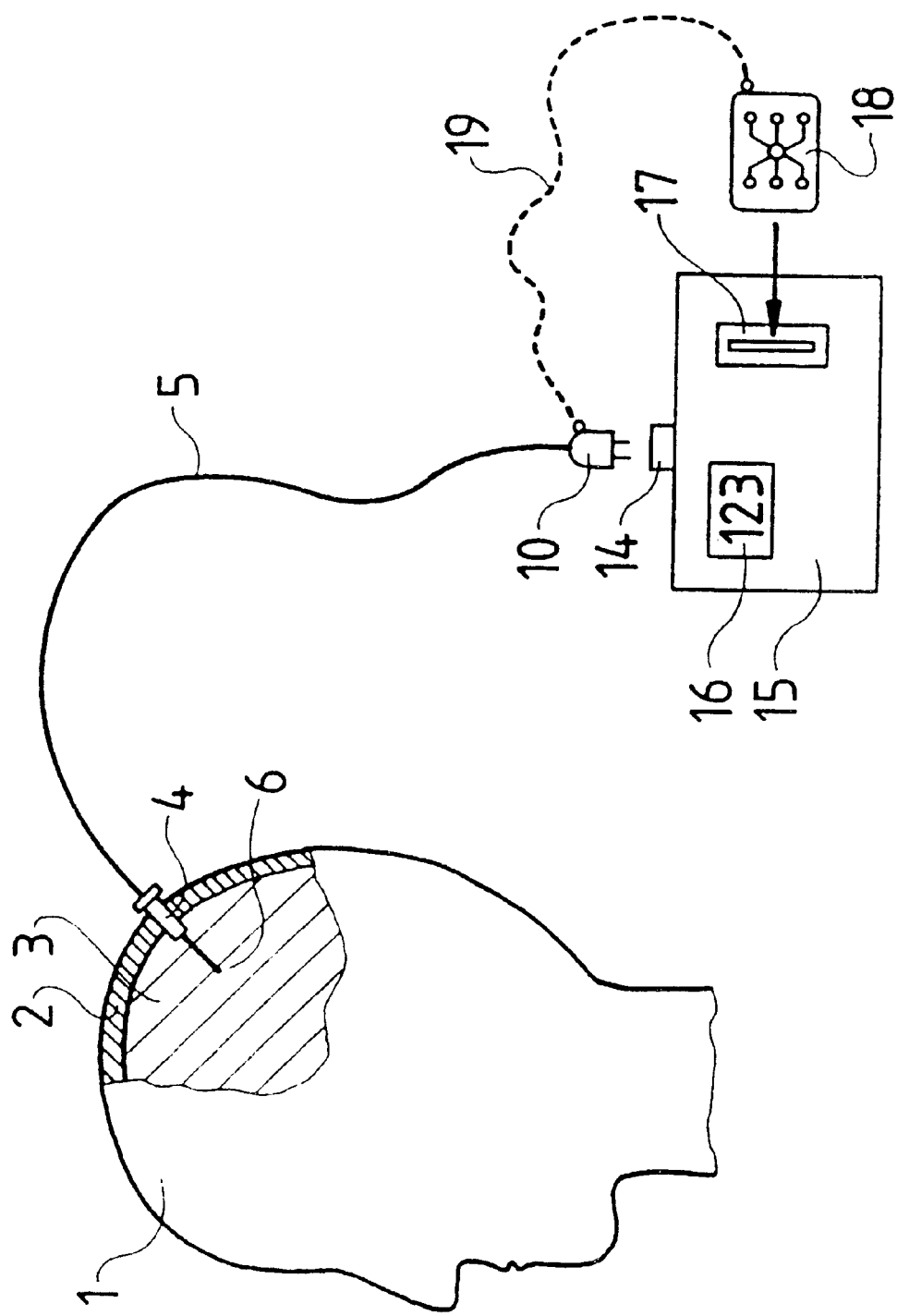
FIG. 1 is a partial section of a patient's head together with measuring apparatus of the invention with probe and measurement device.

FIG. 1 is a partial section of a patient's head 1, with cranium 2 and brain tissue 3.

An insertion fitting 4 is inserted, for instance screwed into a borehole in the cranium 2. A probe 5 is introduced through the insertion fitting 4 into brain tissue 3 as far as a measurement site 6. Insertion fitting 4 may be designed to introduce several probes and illustratively it may also receive an additional, but not shown, pressure probe for determining the inner brain pressure.

Figure 2:
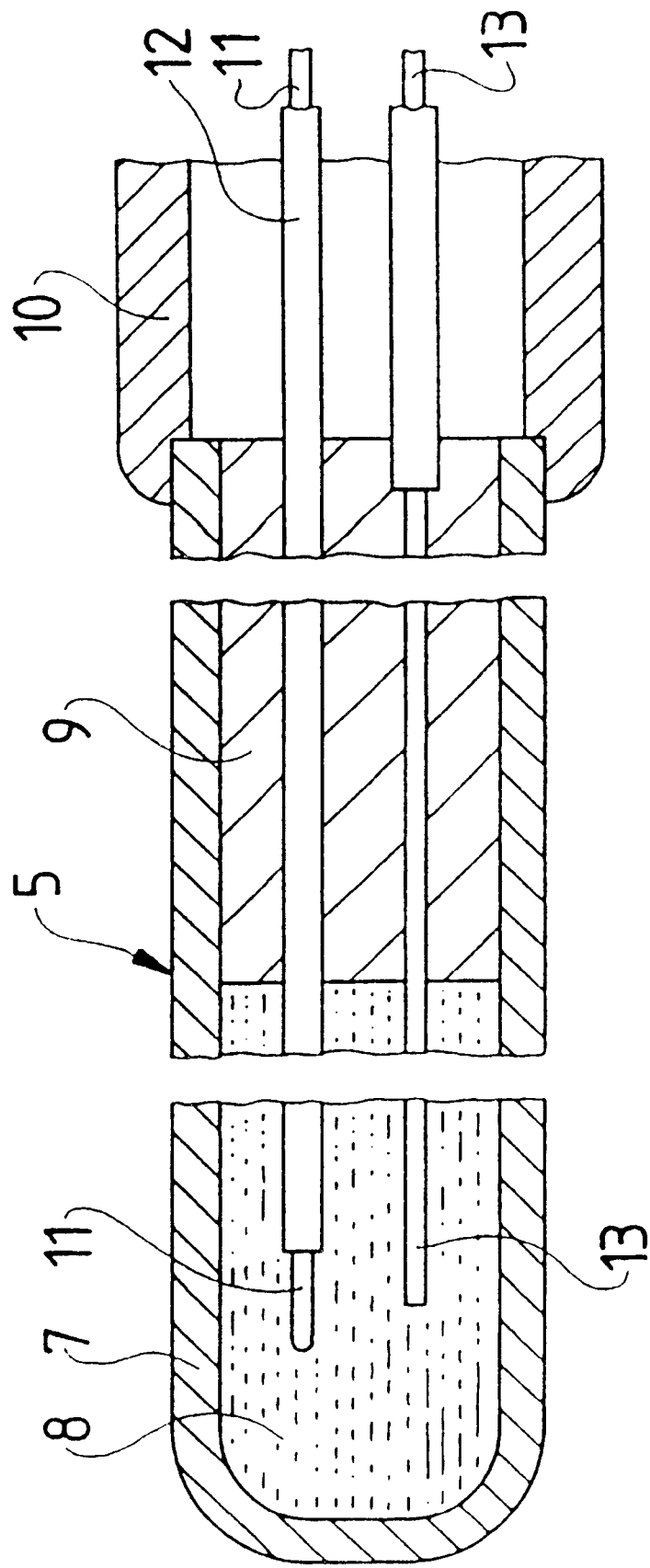
FIG. 2 is an axial section of the probe of the measuring apparatus of FIG. 1.

The shown probe 5 is used to determine the partial oxygen pressure in brain tissue 3 at measurement site 6. The probe is shown in section in FIG. 2.

Probe 5 is designed as a $PO_2$ probe operating on the Clark principle. It comprises an enclosing tube 7 comprising an oxygen diffusing membrane and illustratively made of polyethylene. Illustratively, the tube has an outside diameter of 0.6 mm and a wall thickness of 0.1 mm. The front measurement zone of the probe 5 is filled throughout a length of several cm with an electrolyte 8, preferably an aqueous solution of sodium acetate, sodium phosphate, acetic acid and sodium dihydrogen phosphate to form a wide buffer range able to keep the electrolyte pH constant long-term.

In the remaining length of, for instance, 200 mm, tube 7 is sealed with a casting substance 9. An electric plug 10 is mounted on the outer end of the tube. A cathode 11, for instance of platinum or gold and which is bare in the end zone shown and fitted with insulation 12 over the remaining length, and a silver anode 13, extend from plug 10 into the electrolyte space.

Alternatively, the tube may be filled with electrolyte for instance over its full length, only a short end zone being sealed with casting material 9. Essentially the same conditions result as for a minute electrolyte space because the electrochemical process takes place only in the immediate vicinity of the cathode. Because of the long diffusion paths, more remote zones of an elongated, larger electrolyte space do not participate in the process.

By means of its plug 10, the probe 5 can be connected to the jack 14 of a measuring apparatus 15. As shown in FIG. 1, measuring apparatus 15 comprises a display 16, a reading device 17 with an insertion slot for a data medium 18 which, in the shown and simplified schematic embodiment, is secured by a chain 19 to plug 10 of probe 5.

The data medium 18 may be any commercial read-write device such as is presently conventional for instance in the form of a credit or a phone card. FIG. 1 shows a data medium 18 with an electronic memory chip and electrical contacts. Data medium 18 also may be fitted with a magnetic surface or with a magneto-optical recording surface. Reading device 17 is used to write data into and read them out of data medium 18 and is selected to match the data medium type. In the simplest case, read device 17 may be a floppy disk readout device and the data medium 18 may be a corresponding disk, for instance a 3½" disk.

The data medium may be secured to probe 5 otherwise than shown in this embodiment. For instance, the data medium may be integrated into plug 10, in which case jack 14 must be a read/write device.

Figure 3:
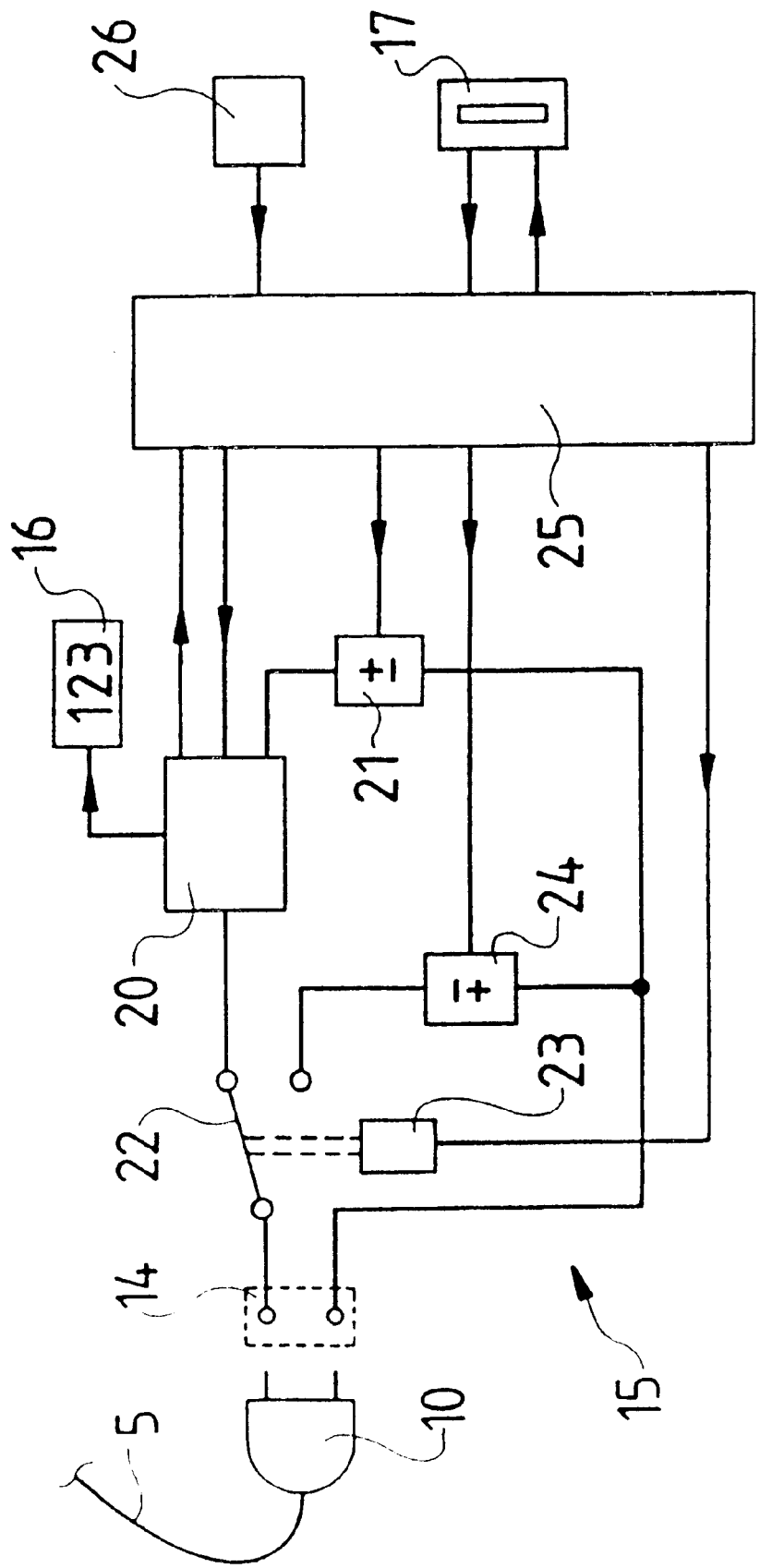
FIG. 3 is a functional block diagram of the measuring apparatus of FIG. 1.

The electronics of measuring apparatus 15 is shown as a functional block diagram in FIG. 3.

When plug 10 is connected to jack 14 and data medium 18, not shown in FIG. 3, is inserted into read device 17, the measuring apparatus is operational. FIG. 3 shows it in its operating state. Probe 5 is connected through a closed circuit and a measurement amplifier 20 to a polarograph power source 21. Polarograph power source 21 sets up a current in probe 5 between cathode 11 and anode 13 and the magnitude of this current is determined in measurement amplifier 20 and displayed at display 16 through appropriate leads (not shown individually in FIG. 3 for the sake of simplification). Instead of being shown by the display 16, the measured current magnitude may be fed (also in a manner not shown) to an external device such as a central computer facility or other analytical means, or recorders etc.

A reversing switch 22 is in the circuit from jack 14 to measurement amplifier 20 and can be moved by a reversing control 23 between switching positions. It is shown in the measurement position in FIG. 3. When this switch is moved into the other, namely the regeneration position, the probe is connected directly to a regeneration power source 24 which, as shown by the polarities indicated at power sources 21 and 24 of FIG. 3, applies a voltage of reversed polarity to probe 5. Consequently, a current is created in the electrolyte between the cathode 11 and the anode 13 which is in the direction opposite that for measurement, whereby the chemical processes are reversed and the electrolyte is regenerated.

Switching between the regeneration and measurement modes illustratively can be implemented automatically at predetermined time intervals or it may be carried out manually using switches, not shown, mounted outside measuring apparatus 15.

A central control unit 25 is shown in the embodiment of measuring apparatus 15 and is connected through data and control leads to the remaining functional elements of this apparatus. An arrow at each lead indicates the direction of flow of the data or control signals. Control unit 25 is connected through a transmit/receive line to read device 17. This read device can receive a large number of data to be used in measurement. Illustratively such data are the probe's manufacturing data such as calibration data relating to a particular probe. These data can be stored by the probe manufacturer in data medium 18. These probe-specific data are fed, after suitable preparation by control unit 25, through a data transmission line to measurement amplifier 20 so that this amplifier appropriately corrects the measured value.

Moreover, data medium 18 may store patient-specific data (name, age etc) which optionally can be displayed on display 16.

A data receiving lead also extends from measurement amplifier 20 to control unit 25. Accordingly, the measured data can be continuously stored in data medium 18, for instance to be retrieved from it later. Moreover, control unit 25 can continuously store the measurement times of probe 5 in data medium 18 in order to ascertain at will and any time the age of the probe and thus the permissible service life.

Because data medium 18 is secured for instance by chain 19 or in other ways to probe 5, this probe can be operated in conjunction with different measuring apparatus any of which can make use of the data storage in data medium 18. In this manner the probe may operate as if it were never separated from the measuring apparatus.

In the shown embodiment, control unit 25 by means of appropriate control leads also controls reversal unit 23 between the measurement and regeneration modes and further controls polarograph plower source 21 and regeneration power source 24 as needed.

Control unit 25 also can control the voltages from polarograph power source 21 and regeneration power source 24 or, in the case of regeneration power source 24, it may control its output current. In an alternative design, the current from regeneration power source 24 when in a suitable circuit can pass through measurement amplifier 20 so said amplifier can monitor the regeneration.

During the measurement mode, control unit 25 receives continuously the information on the magnitude of the measurement current from measurement amplifier 20 and further it receives a time signal from a timer 26. From these data said control unit can calculate the electrolyte consumption, for instance as an integral of the measurement current over time. Using predetermined limit values of electrolyte consumption which the control unit, for instance, reads from data medium 18, it can determine the time at which the electrolyte is exhausted and then car switch to the regeneration mode. In similar manner control unit 25 can determine duration and current magnitude and, following adequately regenerated amount of electrolyte, it can switch back to the measurement mode.

If during the measurement or the regeneration modes probe 5 must be disconnected for medical or administrative reasons from measuring apparatus 15, for instance when putting the patient in another bad, then the status up to that time is stored in the data medium 18 and, upon having moved the patient, probe 5 can be re-connected to the same or another measuring apparatus which then, by means of the data in data medium 18, can proceed exactly from the status just before its operation was interrupted.

As already mentioned, control unit 25 can use read device 17 to continuously store data in data medium 18 or store them in a temporary memory, or only as needed when probe 5 is about to be disconnected. Again it can retrieve the data individually from the data medium as needed, or upon connection of probe 5 it may fully retrieve such data and load them into a buffer memory of its own.

What is claimed is:

1. A measuring apparatus for determining, partial oxygen pressure in human brain tissue (3) comprising a probe (5) dimensioned to be inserted in brain tissue, said probe comprising a thin, flexible tube of a tissue-compatible, oxygen-permeable plastic and having an interior volume;

a liquid electrolyte comprising an acetate in said volume;

a polaragraphic cathode (11) with a limited exposed surface and an anode (13) with a silver surface in said volume and immersed in said electrolyte;

measuring means (15) comprising a power source (21), means for selectively connecting said power source in a polaragraphic mode with a first polarity to said anode and cathode to generate a polaragraphic voltage, a measurement amplifier (20) for determining the magnitude of a current flowing between said anode and cathode in said polaragraphic mode, and a regeneration device (24) for calculating, on the basis of said measured polaragraphic current, a time, duration and current magnitude for regeneration and for applying in a regeneration mode a voltage to said anode and cathode in a polarity reversed from that in said polaragraphic mode for a selected time interval to regenerate said probe; and removable memory means fixedly attached to said probe for recording data from said probe wherein said measuring means records operational data in said polaragraphic mode in an interval immediately preceding disconnection of said probe from said measuring means whereby a patient having a probe inserted can move from one measuring apparatus to another taking said memory means along.

2. A measuring apparatus according to claim 1 wherein said electrolyte comprises a first buffer system comprising acetate in mixture with acetic acid and a second buffer system comprising phosphate in mixture with dihydrogen phosphate.

* * * * *